US012582322B2

(12) United States Patent
Yoshida et al.

(10) Patent No.: US 12,582,322 B2
(45) Date of Patent: Mar. 24, 2026

(54) SPHYGMOMANOMETER MAIN BODY AND SPHYGMOMANOMETER

(71) Applicant: OMRON HEALTHCARE Co., Ltd., Muko (JP)

(72) Inventors: Hideaki Yoshida, Kyoto (JP); Takehiro Hamaguchi, Kyoto (JP); Hiroko Yoshino, Kyoto (JP); Kengo Nishiyama, Kyoto (JP); Asa Hirasawa, Kyoto (JP); Shinya Tanaka, Kyoto (JP); Motofumi Nakanishi, Kyoto (JP); Kazuya Murase, Kyoto (JP); Mika Ezoe, Kyoto (JP); Kenji Ono, Kyoto (JP)

(73) Assignee: Omron Healthcare Co., LTD., Muko (JP)

( * ) Notice: Subject to any disclaimer, the term of this patent is extended or adjusted under 35 U.S.C. 154(b) by 642 days.

(21) Appl. No.: 16/774,370

(22) Filed: Jan. 28, 2020

(65) Prior Publication Data

US 2020/0237239 A1 Jul. 30, 2020

(30) Foreign Application Priority Data

Jan. 30, 2019 (JP) ................................. 2019-014375

(51) Int. Cl.
A61B 5/021 (2006.01)
A61B 5/00 (2006.01)
(Continued)
(52) U.S. Cl.
CPC ...... A61B 5/02141 (2013.01); A61B 5/02225 (2013.01); A61B 5/25 (2021.01);
(Continued)

(58) Field of Classification Search
CPC ... A61B 5/02141; A61B 5/02225; A61B 5/25; A61B 5/316; A61B 5/6824;
(Continued)

(56) References Cited

U.S. PATENT DOCUMENTS

2011/0224561 A1* 9/2011 Ashida ................... A61B 5/022
600/493
2011/0264160 A1* 10/2011 Lenz ...................... A61B 5/332
607/30
(Continued)

FOREIGN PATENT DOCUMENTS

JP 5641011 B2 12/2014
JP 2017-176340 A 10/2017

*Primary Examiner* — Tse W Chen
*Assistant Examiner* — Joseph A Tombers
(74) *Attorney, Agent, or Firm* — Oliff PLC

(57) ABSTRACT

In a main body of an upper-arm type sphygmomanometer that measures blood pressure of a subject by using a bag-shaped arm cuff to be wound around an arm of the subject, a main body housing includes an upper surface, and a first side surface and a second side surface on left and right sides. The first side surface includes a first side surface electrode region, the second side surface includes a second side surface electrode region, the upper surface includes a first upper surface electrode region, a first electrocardiogram waveform measurement electrode is provided in the first side surface electrode region, a second electrocardiogram waveform measurement electrode is provided in the second side surface electrode region, and a first reference electrode is provided in the first upper surface electrode region.

11 Claims, 9 Drawing Sheets

(51) Int. Cl.

| | | |
|---|---|---|
| *A61B 5/022* | (2006.01) | |
| *A61B 5/25* | (2021.01) | |
| *A61B 5/316* | (2021.01) | |

(52) U.S. Cl.
CPC ............ *A61B 5/316* (2021.01); *A61B 5/6824* (2013.01); *A61B 5/7235* (2013.01); *A61B 2562/0247* (2013.01)

(58) Field of Classification Search
CPC .......... A61B 5/7235; A61B 2562/0247; A61B 5/332; A61B 5/6825; A61B 2505/07; A61B 2560/0468; A61B 2562/0209; A61B 5/0225; A61B 5/02208
See application file for complete search history.

(56) References Cited

U.S. PATENT DOCUMENTS

| | | | |
|---|---|---|---|
| 2013/0281868 A1* | 10/2013 | Kawachi ............ | A61B 5/14552 600/485 |
| 2013/0317318 A1* | 11/2013 | Tartz ................... | A61B 5/7225 600/301 |
| 2018/0206736 A1* | 7/2018 | Lee .................... | A61B 5/02125 |
| 2018/0220923 A1* | 8/2018 | Shim ...................... | A61B 5/742 |
| 2020/0229765 A1* | 7/2020 | Peabody ............. | A61B 5/6831 |

* cited by examiner

SPHYGMOMANOMETER MAIN BODY AND SPHYGMOMANOMETER

CROSS-REFERENCE TO RELATED APPLICATIONS

The present invention claims the priority of Japanese Patent Application No. 2019-014375 filed on Jan. 30, 2019, the entire content of which is hereby incorporated by reference.

TECHNICAL FIELD

The present invention relates to a sphygmomanometer main body having an electrocardiogram waveform measurement function and a sphygmomanometer including the sphygmomanometer main body.

BACKGROUND ART

A sphygmomanometer that measures both blood pressure and an electrocardiogram waveform of a subject has been proposed in Patent Document 1 (JP-A-2017-176340). This sphygmomanometer includes a blood pressure measurement unit including an arm cuff and an electrocardiogram waveform measurement unit including a pair of electrodes. Therefore, the subject measuring the blood pressure with the arm cuff attached to his/her arm can measure the electrocardiogram waveform at the same time by touching the pair of electrodes by his/her hands.

In addition, a sphygmomanometer is proposed in Patent Document 2 (U.S. Pat. No. 5,641,011) that measures both the blood pressure and electrocardiogram waveform of a subject and includes an electrode for removing, from the electrocardiogram waveform, environmental noise from a power source, a monitor, Wi-Fi (registered trademark), and the like. This sphygmomanometer includes a pulse wave sensor, and an electrocardiogram waveform measurement unit including a pair of electrocardiogram waveform measurement electrodes and a pair of the noise removal electrodes. This enables a subject to measure his/her blood pressure by touching the pulse wave sensor with a part of his/her hand, and at the same time measure the electrocardiogram waveform with the reduced noise with his/her finger touching the pair of electrodes.

However, with the device described in Patent Document 1 (JP-A 2017-176340), the environmental noise may be transmitted to the electrocardiogram waveform measurement unit through the subject, to hinder accurate measurement of the electrocardiogram waveform.

On the other hand, with the device described in Patent Document 2 (U.S. Pat. No. 5,641,011), the noise removing electrodes are provided so that the electrocardiogram waveform can be measured with the environmental noise reduced. However, to measure the blood pressure, the subject needs to take an unstable posture which is likely to lead to a change in a state of contact between the hand of the subject and the electrocardiogram waveform measurement electrodes. The change in the state of contact is reflected on the electrocardiogram waveform as noise. Furthermore, the blood pressure value obtained is a value estimated from pulse waves which may not accurate, and no structure for accurately measuring the blood pressure value is taken into consideration.

SUMMARY OF THE INVENTION

Therefore, an object of the present invention is to provide an upper-arm sphygmomanometer having an electrocardiogram waveform measurement function capable of accurately measuring both a blood pressure value and an electrocardiogram waveform.

To achieve this object, a main body of an upper-arm type sphygmomanometer that measures blood pressure of a subject by using a bag-shaped arm cuff to be wound around an arm of the subject according to an embodiment of the present disclosure includes:

a housing;

an electrocardiogram waveform measurement circuit provided inside the housing;

a first electrocardiogram waveform measurement electrode and a second electrocardiogram waveform measurement electrode that are provided on an outer surface of the housing, and are electrically connected to the electrocardiogram waveform measurement circuit; and a first reference electrode electrically connected to the electrocardiogram waveform measurement circuit, wherein the housing includes an upper surface, a front surface, a back surface, and a pair of a first side surface and a second side surface on left and right sides, the first side surface includes a first side surface electrode region, the second side surface includes a second side surface electrode region, the upper surface includes a first upper surface electrode region positioned closer to the first side surface than the second side surface, the first electrocardiogram waveform measurement electrode is provided in the first upper surface electrode region, the second electrocardiogram waveform measurement electrode is provided in the second side surface electrode region, the first reference electrode is provided in the first side surface electrode region, and the first electrocardiogram waveform measurement electrode and the first reference electrode are provided at positions to be simultaneously touchable by one hand of the subject.

A main body of an upper-arm type sphygmomanometer that measures blood pressure of a subject by using a bag-shaped arm cuff to be wound around an arm of the subject according to another embodiment includes:

a housing;

an electrocardiogram waveform measurement circuit provided inside the housing;

a first electrocardiogram waveform measurement electrode and a second electrocardiogram waveform measurement electrode that are provided on an outer surface of the housing, and are electrically connected to the electrocardiogram waveform measurement circuit; and a first reference electrode electrically connected to the electrocardiogram waveform measurement circuit, wherein the housing includes an upper surface, a front surface, a back surface, and a pair of a first side surface and a second side surface on left and right sides, the first side surface includes a first side surface electrode region, the second side surface includes a second side surface electrode region, the upper surface includes a first upper surface electrode region positioned closer to the first side surface than the second side surface, the first electrocardiogram waveform measurement electrode is provided in the first upper surface electrode region, the second electrocardiogram waveform measurement electrode is provided in the second side surface electrode region, the first reference electrode is provided in the first side surface electrode region, and the first electrocardiogram waveform measurement electrode and the first reference electrode are provided at positions to be simultaneously touchable by one hand of the subject.

An upper-arm type sphygmomanometer according to an embodiment of the present disclosure includes:

a sphygmomanometer main body; and an arm cuff unit that is detachably attached to the sphygmomanometer main body, wherein the sphygmomanometer main body is the sphygmomanometer main body according to the other embodiment, the arm cuff unit includes a belt-shaped arm cuff incorporating an air bladder, and an air tube that has one end connected to the air bladder, and supplies air to the air bladder, the sphygmomanometer main body includes a tube connection portion to which another end of the air tube is detachably connected, the tube connection portion being provided on a surface of the housing, and the tube connection portion is connected to the air supply circuit.

BRIEF DESCRIPTION OF THE DRAWINGS

The present invention will become more fully understood from the detailed description given herein below and the accompanying drawings which are given by way of illustration only, and thus are not limitative of the present invention, and wherein.

EMBODIMENTS OF THE INVENTION

Hereinafter, an embodiment of an upper-arm sphygmomanometer according to the present invention will be described with reference to the accompanying drawings.

[1: Upper-Arm Sphygmomanometer]

Figure 1:
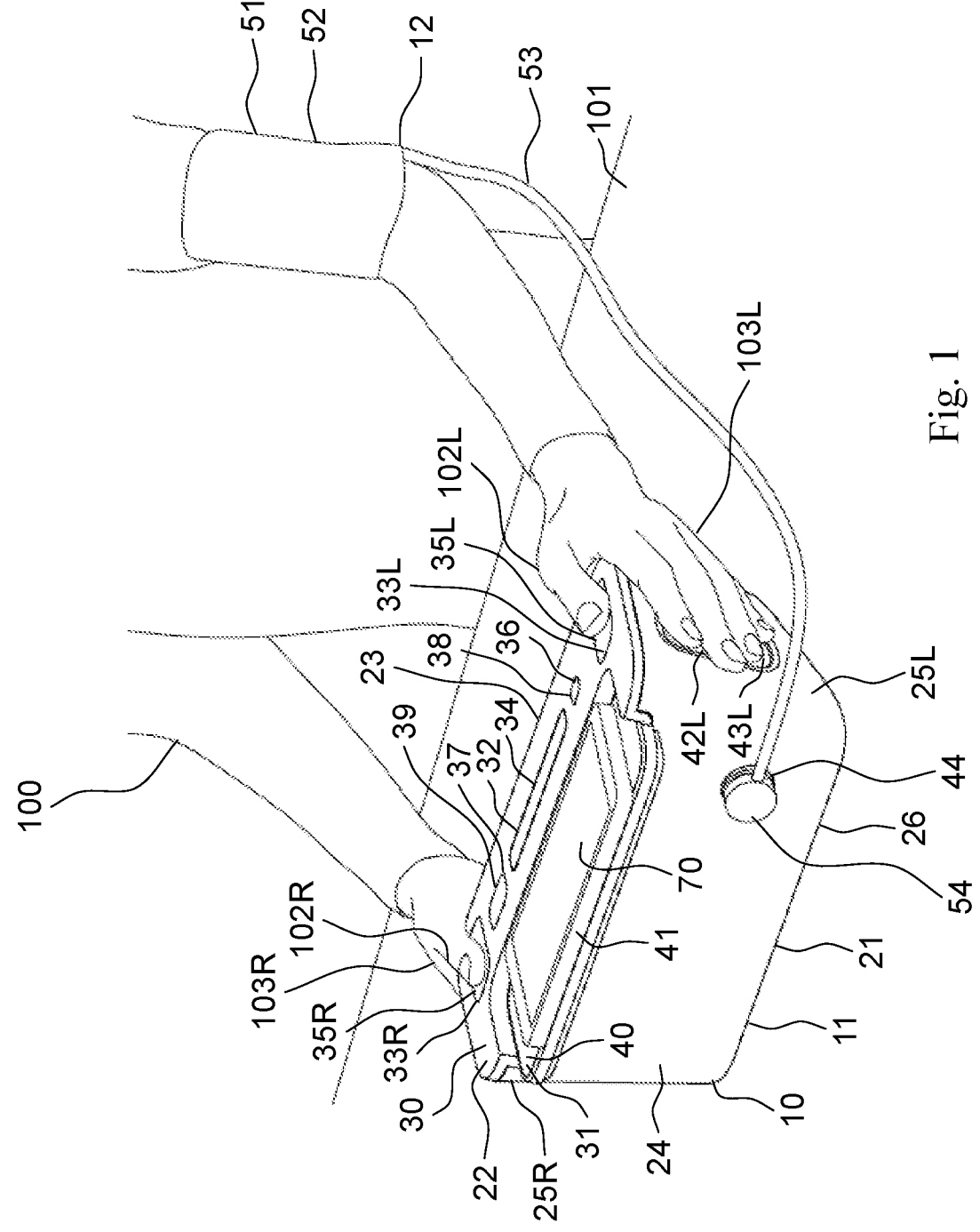
FIG. 1 is a perspective view illustrating an upper-arm type sphygmomanometer according to an embodiment of the present invention and a used state thereof.

FIG. 1 illustrates a schematic configuration of an upper-arm sphygmomanometer (hereinafter, appropriately referred to as a □sphygmomanometer□) 10 according to an embodiment of the present invention. The sphygmomanometer 10 is a sphygmomanometer with an electrocardiogram waveform measurement function having a function of measuring the blood pressure and an electrocardiogram waveform of the subject 100.

[2: Configuration of Upper-Arm Sphygmomanometer]

As illustrated in FIG. 1, the sphygmomanometer 10 has a sphygmomanometer main body 11 and an arm cuff unit 12.

The sphygmomanometer main body 11 has a housing 21 incorporating various control devices to be described later. In the embodiment, the housing 21 has a box shape that is long in a lateral direction, and has an outer shape defined by an upper surface 22, a front surface 23, a back surface 24, left and right side surfaces 25 (25L, 25R), and a bottom surface 26.

Figure 2:
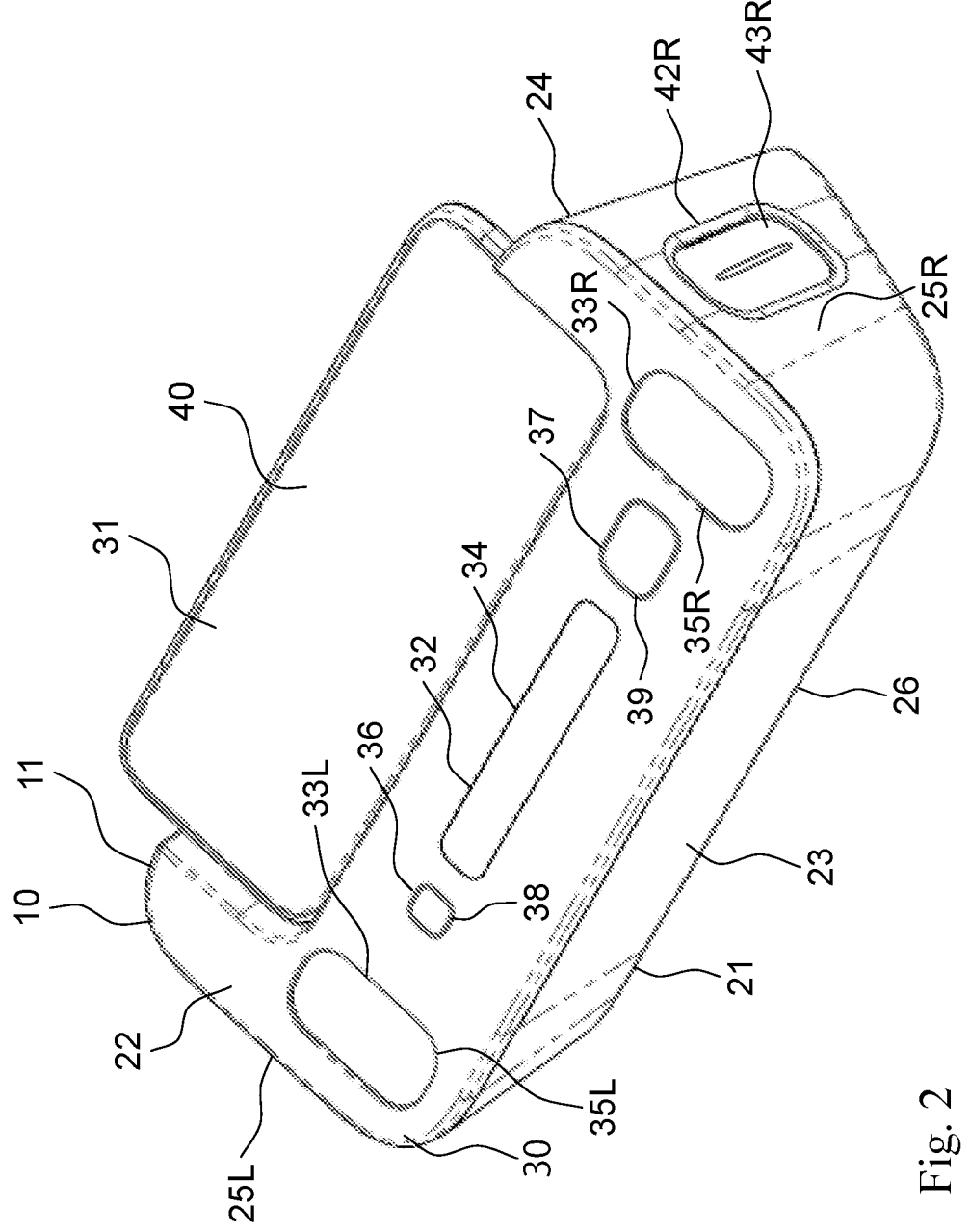
FIG. 2 is a perspective view of an upper-arm type sphygmomanometer main body illustrated in FIG. 1 as viewed from obliquely above.

In the embodiment, the upper surface 22 is inclined as a whole to have a height gradually increasing from the front surface 23 toward the back surface 24. A first interface region (man-machine interface region) 30 is disposed on the front surface 23 side. A second interface region (man-machine interface region) 31 is arranged on the back surface 24 side (see FIG. 2).

The first interface region 30 includes a display region 32 at the center in a left and right direction, and a pair of upper surface electrode regions (first and second upper surface electrode regions) 33 (33L and 33R) disposed on both sides of the display region 32 to be close to the left and right side surfaces 25 (25L and 25R). The central display region 32 has a laterally long rectangular shape, and has a display unit 34 arranged therein. Preferably, the display unit 34 is formed by a liquid crystal display. In the embodiment, the left and right upper surface electrode regions 33 have a vertically long rectangular shape that is long in a front and rear direction, and have reference electrodes 35 (a first reference electrode 35L and a second reference electrode 35R) arranged therein. The reference electrode 35 has at least a surface formed of a conductive material, to be a portion the subject 100 touches with his/her body part (specifically, at least a right or left thumb 102 as illustrated in FIG. 1) when measuring the electrocardiogram waveform, to remove the noise that may otherwise be included in the electrocardiogram waveform.

The first interface region 30 includes, in addition to the display unit 34 and the reference electrodes 35, switch regions 36 and 37 that are respectively formed between the display unit 34 and the left electrode 35 and between the display unit 34 and the right electrode 35, and are respectively provided with a communication switch 38 and a start/stop switch 39.

In the embodiment, the second interface region 31 has a back surface side upper surface portion at a lower level than a front interface side upper surface portion provided with the first interface region 30. In the back surface side upper surface portion, a portable information terminal placement portion 40 that is flat and has a laterally long rectangular shape to be long in the left and right direction is formed. The portable information terminal placement portion 40 is a region where a portable information terminal 41 (for example, a smartphone) is placed. Therefore, the portable information terminal placement portion 40 is sized and shaped to be capable of stably supporting a commercially available portable information terminal of a normal size. In the embodiment, the portable information terminal placement portion 40 has a back end protruding backward from the back surface 24 of the housing 21 so as to be capable of supporting the entirety of the largest portable information terminal available on the market. Furthermore, the surface of the portable information terminal placement portion 40 is inclined so as to have a height gradually increasing toward the back side.

Both side surfaces 25 (25L, 25R) of the housing 21 have respective side electrode regions 42 (first and second side electrode regions 42L and 42R) that are provided with respective electrocardiogram waveform measurement electrodes (a first electrocardiogram waveform measurement electrode 43L and a second electrocardiogram waveform measurement electrode 43R). The electrocardiogram waveform measurement electrodes 43 each have at least a surface formed of a conductive material, to be a portion the subject 100 touches with his/her body part (specifically, a finger 103 different from the thumb as illustrated in FIG. 1, such as an index finger, a middle finger, and a pinky for example) when measuring the electrocardiogram waveform.

Figure 4:
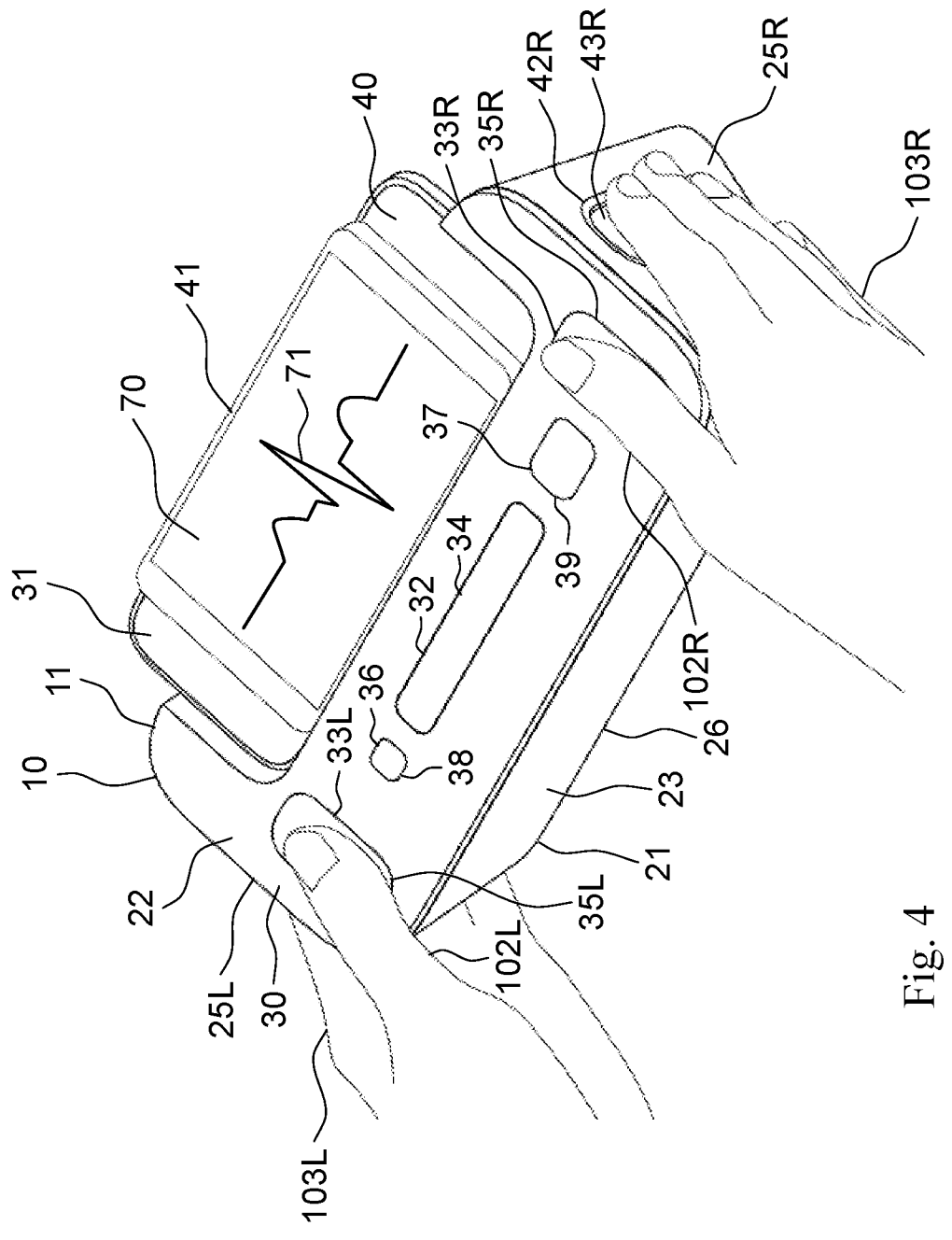
FIG. 4 is a perspective view of the upper-arm type sphygmomanometer main body, on which a portable information terminal is mounted, as viewed from obliquely above.

In a state illustrated in FIGS. 1 and 4 where both arms of the subject 100 are directed forward and placed on a table 101 or the like to measure the electrocardiogram waveform, a tip portion (which is a portion more on the distal side than the first knuckle joint (DIP joint)) of the thumb 102 of the subject 100 generally is more on the closer side (subject side) than a tip portion of the other finger 103 (such as index finger, middle finger, ring finger, or pinky). Therefore, in the embodiment, the reference electrode 35 is placed on the front surface 23 side and the electrocardiogram waveform measurement electrode 43 is disposed closer to the back surface 24 than the reference electrode 35 is, so that the thumb 102 and the other finger 103 can be respectively in contact with the reference electrode 35 and the electrocardiogram waveform measurement electrode 43 without stress, in the state where both arms of the subject 100 are directed forward. The left and right electrocardiogram waveform measurement electrodes 43 are arranged symmetrically with respect to the center axis in the front and rear direction so that the left and right electrocardiogram waveform measurement electrodes 43 receive force in opposite directions on the same line of action.

In a preferred embodiment, the size of the reference electrode 35 (the first reference electrode 35L and the second reference electrode 35R) is 40 mm (length)×23 mm (width), and the size of the electrocardiogram waveform measurement electrode 43 (the first electrocardiogram waveform measurement electrode 43L and the second electrocardiogram waveform measurement electrode 43R) is 50 mm (length)×23 mm (width). The center of the reference electrode 35 is disposed at a position 29 mm away from the front surface 23 in the direction of inclination of the upper surface 22 from the front surface 23 toward the back surface 24, and 22.5 mm away from one of side surface 25 in a horizontal direction from the one side surface 25 (25L, 25R) to the other side surface 25 (25L, 25R). The center of the electrocardiogram waveform measurement electrode 43 is disposed at a position 51.5 mm away from the front surface 23 in the inclination direction of the upper surface 22 from the front surface 23 to the back surface 24, and 39 mm away from the bottom surface 26 in a vertical direction of the upper surface 22 from the upper surface 22 to the bottom surface 26. With the reference electrode 35 and the electrocardiogram waveform measurement electrode 43 thus arranged, as illustrated in FIG. 4, the subject 100 can touch the reference electrode 35 and the electrocardiogram waveform measurement electrode 43 simultaneously respectively with the thumb 102 and the other finger 103 naturally and without stress, in a state where the outer side of the hand is placed on the table 101. Therefore, body motion noise that may be included in the electrocardiogram waveform can be removed.

As illustrated in FIG. 1, the back surface 24 of the housing 21 is provided with an arm cuff tube connection portion (connection hole for air supply) 44.

As illustrated in FIG. 1, the arm cuff unit 12 includes a belt-shaped arm cuff 51 incorporating an air bladder 52, and an air tube 53 having one end connected to the air bladder 52. At the other end of the air tube 53, a connector shaped to be detachable is attached to the arm cuff tube connection portion 44 on the housing back surface 24. The connector 54 is connected to an end of a later described air supply circuit 55 (see FIG. 5) provided inside the housing 21. Therefore, the air bladder 52 is connected to the air supply circuit 55 (see FIG. 5) via the air tube 53 in a state where the connector 54 is connected to the arm cuff tube connection portion 44.

Figure 5:
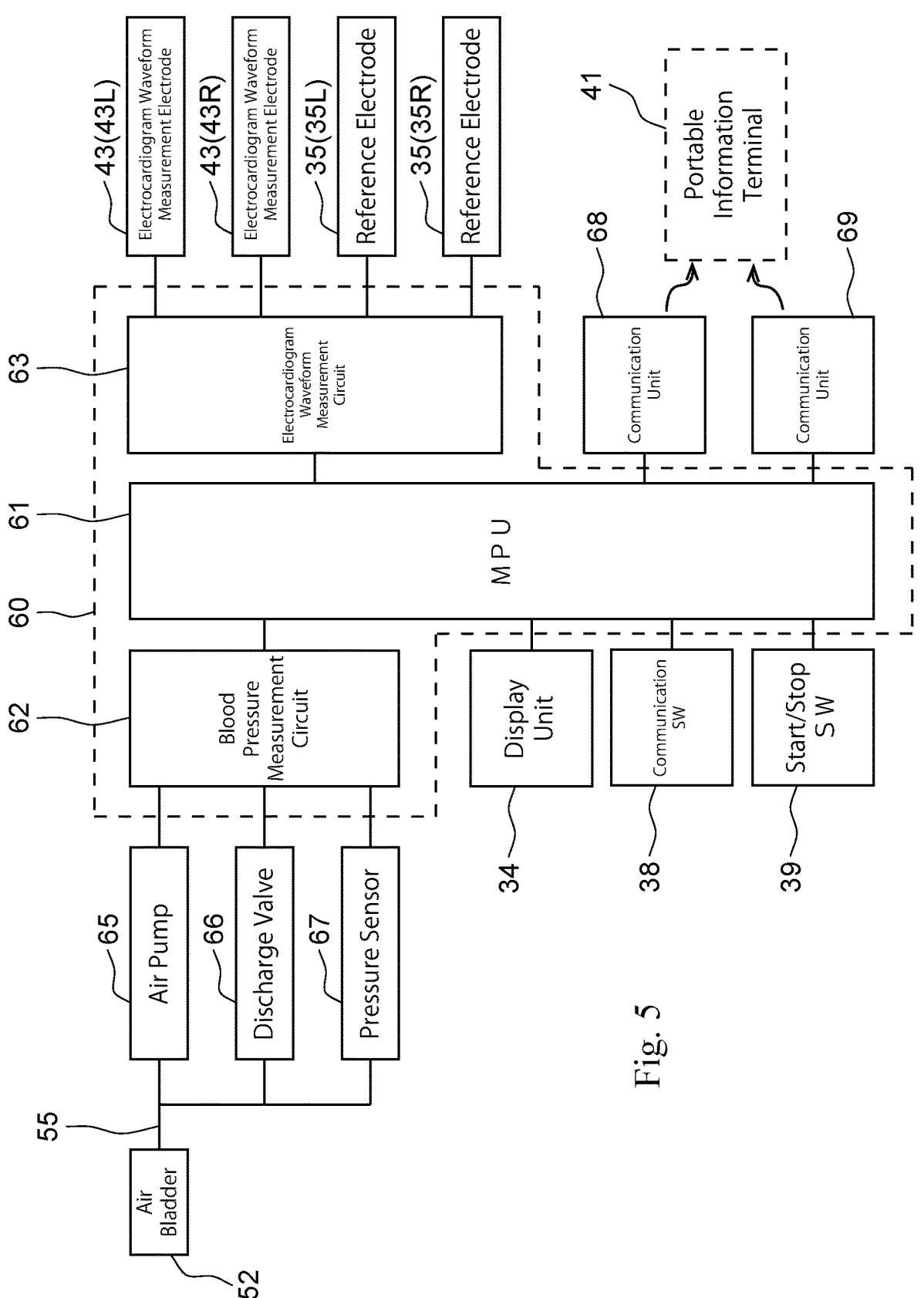
FIG. 5 is a control block diagram of the upper-arm type sphygmomanometer illustrated in FIG. 1.

The housing 21 incorporates a control unit 60 illustrated in FIG. 5. In the embodiment, the control unit includes a processor 61 as well as a blood pressure measurement circuit 62 and an electrocardiogram waveform measuring circuit 63 that are connected to the processor 61 and are respectively communicably connected to a device related to blood pressure measurement, and a device related to electrocardiogram waveform measurement.

The device related to the measurement of blood pressure includes an air pump 65 that supplies air to the air bladder 52 of the arm cuff unit 12 via the air supply circuit 55, a discharge valve 66 for opening the air supply circuit 55 to the atmosphere to discharge the air from the air bladder 52, and a pressure sensor 67 that detects the pressure in the air supply circuit 55.

The device related to the measurement of the electrocardiogram waveform includes the above-described electrocardiogram waveform measurement electrodes 43 (the first electrocardiogram waveform measurement electrode 43L and the second electrocardiogram waveform measurement electrode 43R) and the reference electrodes 35 (the first reference electrode 35L and the second reference electrode 35R).

The processor 61 is electrically connected to the display unit 34, the communication switch 38, and the start/stop switch 39. The processor 61 is configured to output a necessary signal to the display unit 34 in accordance with display contents to be displayed on the display unit 34, and is also configured to receive, when the communication switch 38 and the start/stop switch 39 are pressed, the corresponding signal from each of the communication switch 38 and the start/stop switch 39.

The processor 61 is further electrically connected to a communication unit (blood pressure transmission unit) 68 that wirelessly transmits the blood pressure and pulse rate measured by the blood pressure measurement circuit 62 and a communication unit (electrocardiogram waveform transmission unit) 69 that wirelessly transmits the electrocardiogram waveform measured by the electrocardiogram waveform measurement circuit 63, and is configured to wirelessly transmit the blood pressure and the pulse rate through the communication unit 68 and to wirelessly transmit the electrocardiogram waveform through the communication unit 69.

When measuring blood pressure using the sphygmomanometer configured as described above, as illustrated in FIG. 1, the connector 54 of the arm cuff unit 12 is connected to the arm cuff tube connection portion 44 of the housing 21, and the air bladder 52 is connected to the air supply circuit 55. In addition, the arm cuff 51 of the arm cuff unit 12 is wound around the upper arm of the subject 100. In this state, when the subject 100 presses (turns ON) the blood pressure measurement start/stop switch 39 on the housing upper surface 22, blood pressure measurement starts.

When the blood pressure measurement start/stop switch 39 is pressed (ON), a pressed (ON) signal is detected by the processor 61. When the processor 61 detects the pressed (ON) signal, in response to the signal, the blood pressure measurement circuit 62 drives the air pump 65 to supply air to the air bladder 52 through the air supply circuit 55, so that the upper arm of the subject 100 is compressed by the arm cuff 51. While air is being supplied to the air bladder by the air pump 65, the pressure of the air bladder 52 (this corresponds to the pressure of the air supply circuit 55) is detected by the pressure sensor 67.

When it is detected from the output of the pressure sensor 67 that the pressure of the air bladder 52 has reached a predetermined pressure, the blood pressure measurement circuit 62 opens the discharge valve 66 to discharge the air in the air bladder 52. While the air is being discharged from the air bladder 52, the pressure of the air bladder 52 is detected by the pressure sensor 67.

The output of the pressure sensor 67 is detected by the blood pressure measurement circuit 62. The blood pressure measurement circuit 62 calculates the blood pressure (systolic blood pressure, diastolic blood pressure) and the pulse rate from the output of the pressure sensor 67 based on a predetermined blood pressure calculation algorithm, and outputs the calculation result to the processor 61. The processor 61 outputs and displays the blood pressure and the pulse rate received from the blood pressure measurement circuit 62 to and on the display unit 34.

As will be described later, after the blood pressure measurement, when the communication switch 38 on the housing upper surface 22 is pressed (turned ON), the blood pressure measurement circuit 62 transmits the blood pressure and the pulse rate to the portable information terminal 41 through the communication unit 68.

When an electrocardiogram waveform is measured, the portable information terminal 41 is placed on the portable information terminal placement portion 40 as illustrated in FIG. 1. Dedicated software (application) for receiving the electrocardiogram waveform information output from the sphygmomanometer 10 by the portable information terminal 41 and displaying the received electrocardiogram waveform information on the display of the portable information terminal 41 is installed in the portable information terminal 41. In this state, the subject 100 touches the electrocardiogram waveform measurement electrodes 43 on the left and right sides with his/her fingers 103 (index finger, middle finger, or ring finger) other than the left and right thumbs.

The subject 100 also touches the reference electrode(s) 35 on the upper surface 22 with one of the left and right thumbs 102 or both.

As illustrated in the figure, in this state, the finger 103 other than the thumb is located more on the forward side than the thumb 102. Thus, the sphygmomanometer 10 of the embodiment has the electrocardiogram waveform measurement electrode 43, on the side surface 25, arranged more on the forward side of the subject (away from the subject) than the reference electrode 35 on the upper surface 22. Therefore, the subject 100 can touch the reference electrodes 35 and the electrocardiogram waveform measurement electrodes 43 with the left and right thumbs and other fingers naturally (a state with no stress), and can maintain to be in the state without stress.

When the subject 100 touches the electrocardiogram waveform measurement electrodes 43 with the fingers 103 of both hands, the electrocardiogram waveform measurement circuit 63 detects that the electrocardiogram waveform measurement electrodes 43 are electrically brought into contact with each other through the subject, and is triggered by this detection signal to start the electrocardiogram waveform measurement. In this state, the thumb(s) 102 of one of left and right hands of the subject 100 or both is in contact with the reference electrode(s) 35.

In this state, there is a potential difference between the signal input to the reference electrode 35 and the signal input to the electrocardiogram waveform measurement electrode 43. This potential difference is caused by a difference in length between paths to the thumb 102 and the other finger 103. The signals input to the reference electrode 35 and to the electrocardiogram waveform measurement electrode 43 include noise at substantially the same level. Thus, an electrocardiogram waveform less affected by noise can be obtained by measuring potential difference between the signals input to the reference electrode 35 through the thumb 102 and to the electrocardiogram waveform measurement electrode 43 through the other finger 103, and amplifying the potential difference as appropriate.

Figures 8A, 8B:
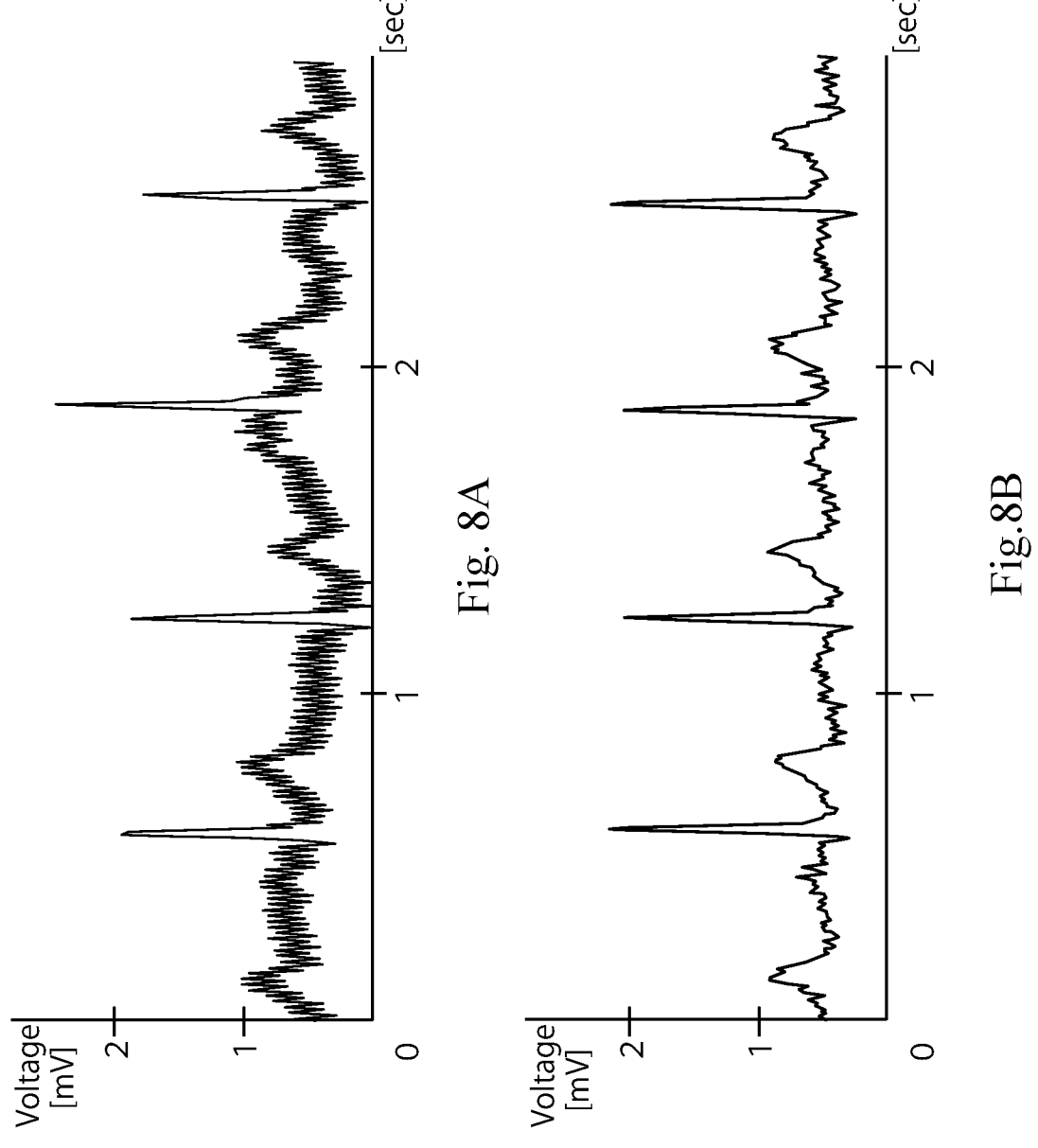
FIG. 8A is an electrocardiogram waveform measured with the reference electrode not touched.
FIG. 8B is an electrocardiogram waveform measured with the reference electrode touched.

The noise reduction effect will be described with reference to FIGS. 8A and 8B. To begin with, FIG. 8A illustrates an electrocardiogram waveform obtained in a state where only the fingers 103 other than the left and right thumbs are in contact with the left and right electrocardiogram waveform measurement electrodes 43 (the left and right thumbs 102 are not touching the reference electrodes 35). FIG. 8B illustrates an electrocardiogram waveform obtained in a state where the fingers 103 other than the left and right thumbs are each touching the corresponding one of the left and right electrocardiogram waveform measurement electrodes 43, and the left or the right thumb 102 is touching the corresponding one of the reference electrodes 35. On the electrocardiogram waveform illustrated in FIG. 8A obtained in a state where the thumb 102 is not touching the reference electrode 35, noise having an amplitude of about 0.2 mV and a frequency of about 60 Hz is imposed. On the other hand, no such noise can be found on the electrocardiogram waveform illustrated in FIG. 8B obtained in the state where the right or left thumb 102 is touching the reference electrode 35. Therefore, it is clear that noise can be removed from the electrocardiogram waveform by bringing one of the left and right thumbs 102 or both into contact with the reference electrode(s) 35.

In addition to the noise removal function described above, with the sphygmomanometer of the above-described embodiment, the subject 100 can naturally touch the sphygmomanometer main body 11 during the measurement of the electrocardiogram waveform, as described above. Thus, the body movement of the subject can be minimized during the measurement of the electrocardiogram waveform (about 30 seconds). Therefore, generation of noise due to body movement can be minimized.

The electrocardiogram waveform thus obtained is transmitted to the portable information terminal 41 through the communication unit 69. As illustrated in FIG. 4, the portable information terminal 41 that has received an electrocardiogram waveform 71 displays it on a display 70 of the portable information terminal 41 in real time in accordance with the installed software. The electrocardiogram waveform information is stored in a memory of the portable information terminal 41 together with other measurement information (measurement date and time). The electrocardiogram waveform information stored in the memory can be transmitted to another communication terminal if needed.

The information about the blood pressure and the pulse rate obtained by the blood pressure measurement is transmitted to the portable information terminal 41 through the communication unit 68 when the communication switch 38 on the upper surface 22 of the housing is pressed (turned ON). The blood pressure and the pulse rate received by the portable information terminal 41 are displayed on the display 70 of the portable information terminal 41 together with the electrocardiogram waveform. As in the case of the electrocardiogram waveform information, the information about the blood pressure and the pulse rate is stored in the memory of the portable information terminal 41 together with other measurement information (measurement date and time). The information about the blood pressure and the pulse rate stored in the memory can be transmitted to another communication terminal if needed.

As described above, with the sphygmomanometer 10 and the sphygmomanometer main body 11 according to the above-described embodiment, the subject 100 can take a relaxed posture to maintain substantially the same contact area and substantially the same contact pressure with the thumbs 102 and the other fingers 103 during the electrocardiogram waveform measurement. In addition, it is possible to minimize noise that may be included in the electrocardiogram waveform, including external noise, noise generated by body movement of the subject 100, and noise caused by a change in the contact pressure or contact area between the electrocardiogram waveform electrode and the finger.

The above-described sphygmomanometer and sphygmomanometer main body can be modified in various ways.

Figure 6:
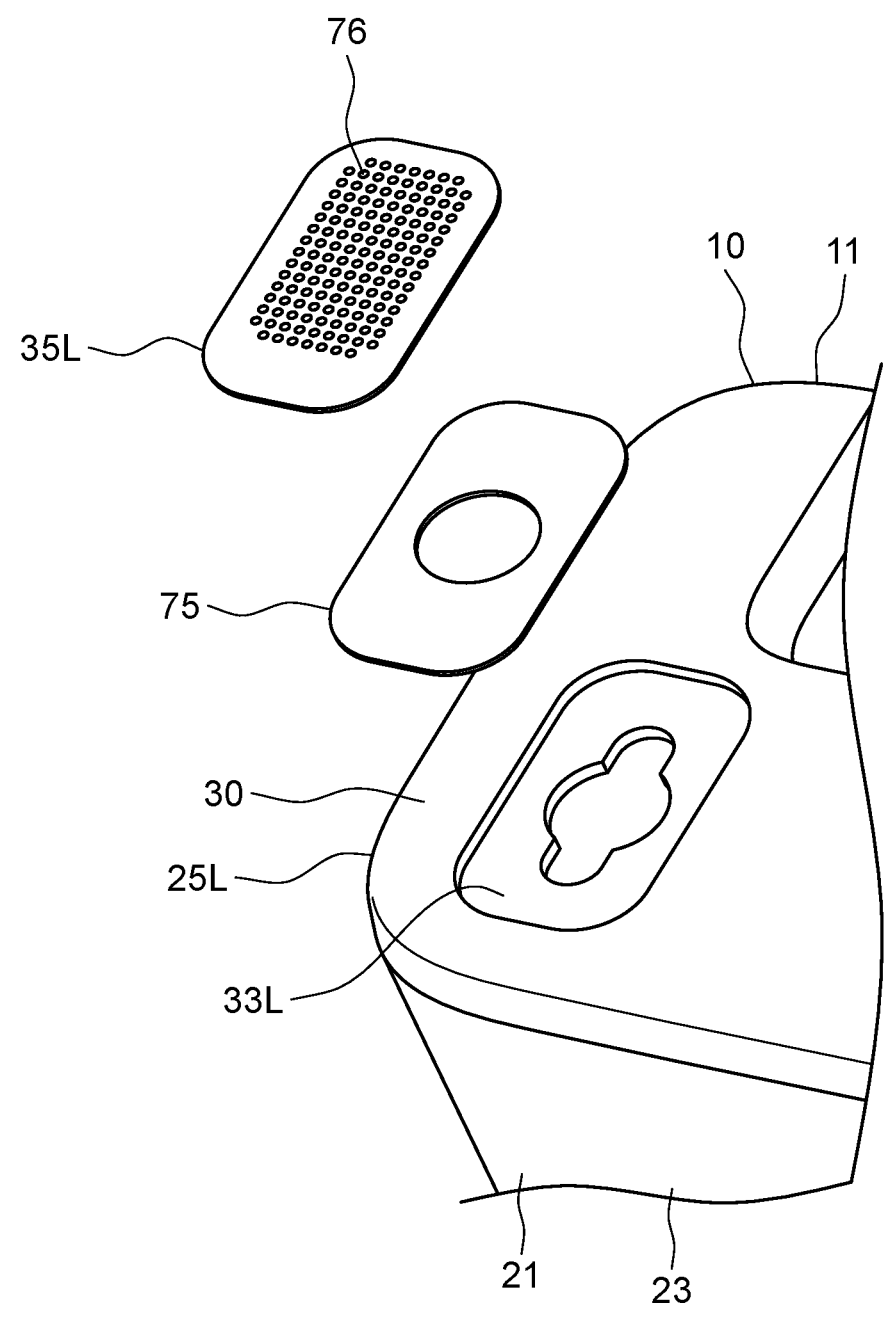
FIG. 6 is an exploded perspective view illustrating a reference electrode and an elastic supporting portion.

For example, as illustrated in FIG. 6, an elastic supporting portion 75 may be provided between the reference electrode 35 and the housing 21. The elastic supporting portion 75 is formed of an insulating elastic sheet or an insulating elastic pad having sufficient elasticity to be easily compressed by force applied to the reference electrode 35. With this configuration, the subject can recognize that his/her finger is in contact with the reference electrode with an appropriate force, in response to the deformation of the elastic supporting portion 75. Furthermore, as illustrated in FIG. 6, one or a plurality of protrusions 76 may be formed on the surface of the reference electrode 35 so that the subject can recognize that his/her finger is in contact with the reference electrode 35.

Figure 3:
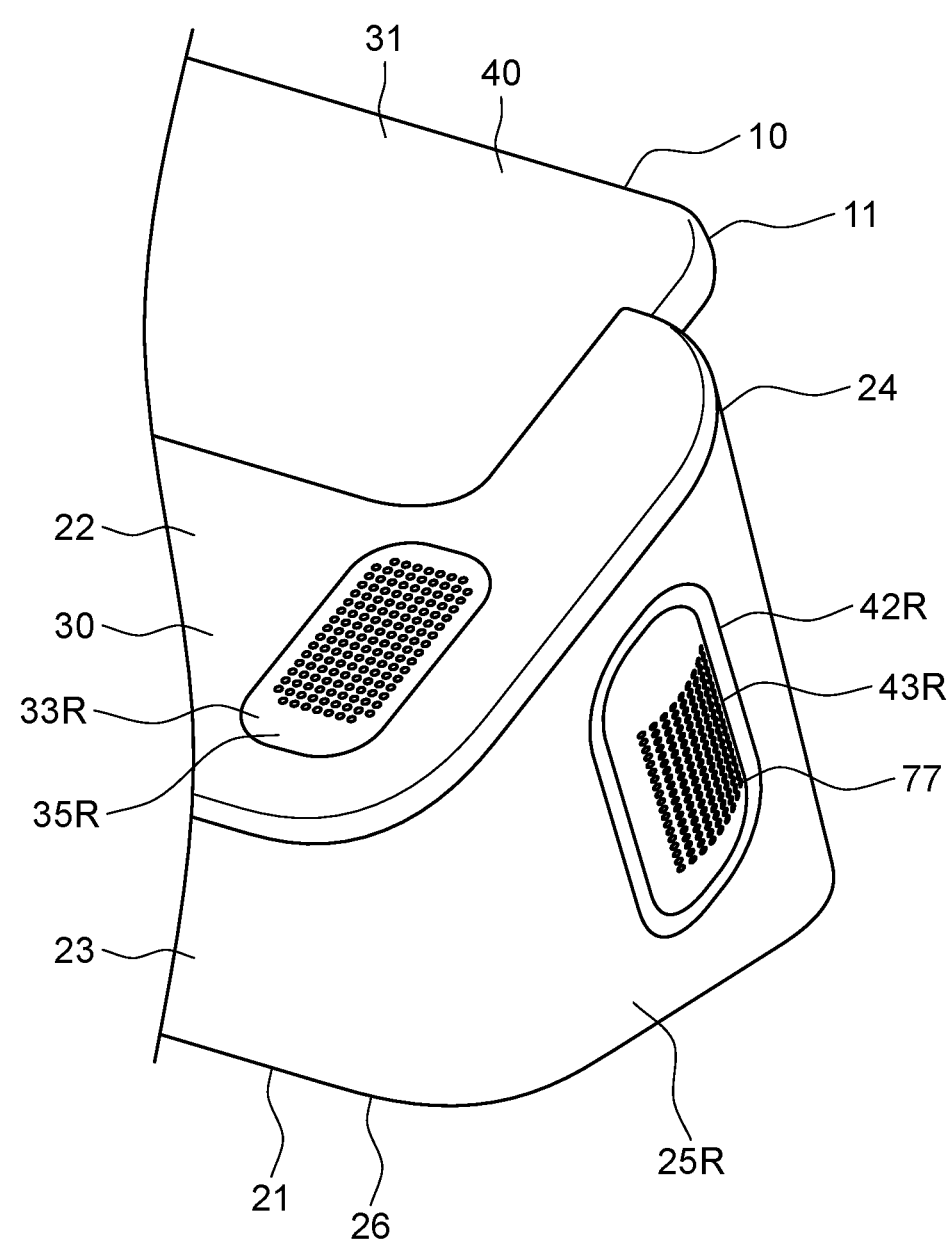
FIG. 3 is a partial perspective view of the upper-arm type sphygmomanometer main body illustrated in FIG. 1 as viewed from obliquely above.

The elastic supporting portion may further be arranged between the electrocardiogram waveform measurement electrode and a portion of the housing supporting the electrocardiogram waveform measurement electrode 43. With this configuration, the subject can recognize that his/her finger is in contact with the electrocardiogram waveform measurement electrode 43 with an appropriate force, in response to the deformation of the elastic supporting portion. Furthermore, as illustrated in FIG. 3, one or a plurality of protrusions 77 may also be formed on the surface of the electrocardiogram waveform measurement electrode 43 so that the subject can recognize that his/her finger is in contact with the electrocardiogram waveform measurement electrode 43.

In the above-described embodiment, the reference electrodes 35 are arranged in the left and right upper surface electrode regions 33, and the electrocardiogram waveform measurement electrodes 43 are arranged in the left and right side surface electrode regions 42. Alternatively, the electrocardiogram waveform measurement electrodes may be arranged in the upper surface electrode regions and the reference electrodes may be arranged in the side electrode regions.

Still, in order to measure an electrocardiogram waveform stably, it is preferable to arrange the reference electrodes in the left and right upper surface electrode regions 33 and to arrange the electrocardiogram waveform measurement electrodes 43 in the left and right side surface electrode regions 42. This is due to the following reason. Specifically, in a state where the hands are placed on the table 101 with the outer sides of hands facing down, the thumb 102 has a higher degree of freedom of movement, to be more likely to move than the finger 103 other than the thumb. Thus, for example, when the thumb 102 is brought into contact with the electrocardiogram waveform measurement electrode 43 provided in the upper surface electrode region 33, the thumb 102 may move to change the contact resistance between the thumb 102 and the electrocardiogram waveform measurement electrode 43.

Figures 9A, 9B:
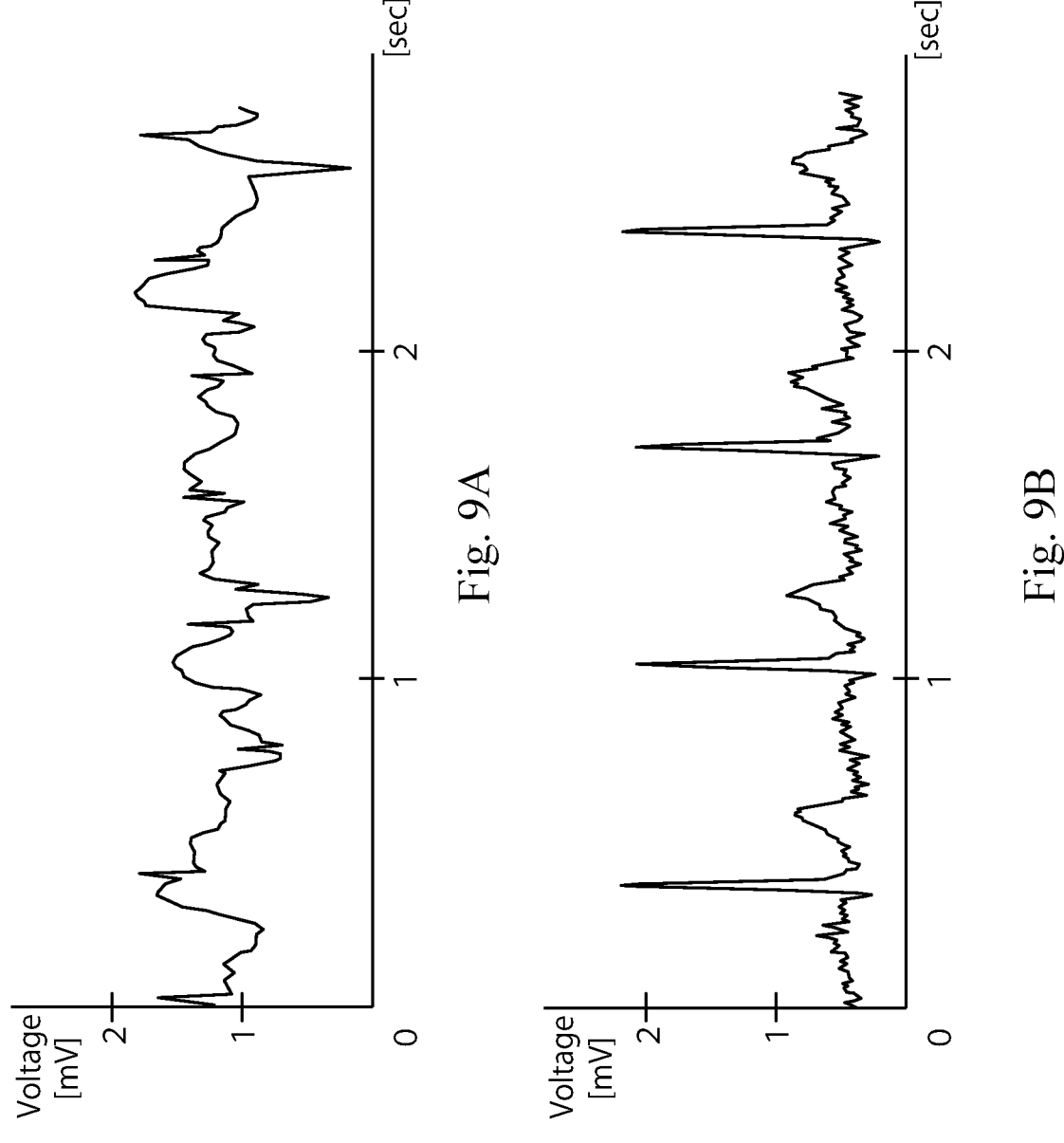
FIG. 9A illustrates an electrocardiogram waveform measured when an electrocardiogram waveform measurement electrode is provided on an upper surface.
FIG. 9B illustrates an electrocardiogram waveform measured when an electrocardiogram waveform measurement electrode is provided on a side surface.

Specifically, as illustrated in FIG. 9A, an electrocardiogram waveform measured by providing the electrocardiogram waveform measurement electrode in the upper surface electrode region is a very unstable waveform with the base line fluctuating. On the other hand, as illustrated in FIG. 9B, an electrocardiogram waveform measured by providing the electrocardiogram waveform measurement electrode in the side surface electrode region is a waveform with no base line fluctuation. Thus, in order to measure an electrocardiogram waveform stably, it is preferable to arrange the reference electrodes 35 in the left and right upper surface electrode regions 33 and to arrange the electrocardiogram waveform measurement electrodes 43 in the left and right side surface electrode regions 42.

Furthermore, for example, one of the pair of reference electrodes may be disposed in the left (or right) upper surface electrode region and the other one of the pair of reference electrodes may be disposed in the right (or left) side surface electrode region, and one of the pair of electrocardiogram waveform measurement electrodes may be disposed in the left (or right) side surface electrode region, and the other one of the pair of electrocardiogram waveform measurement electrodes may be disposed in the right (or left) upper surface electrode region. With this configuration, the electrocardiogram waveform from which the external noise has been removed can be measured even when the left or the right thumb or the finger other than the thumb of the subject is separated from the electrode.

In the above-described embodiment, the left and right fingers are brought into contact with the left and right electrocardiogram waveform measurement electrodes 43, and the resultant detection signal triggers the electrocardiogram waveform measurement. Alternatively, an electrocardiogram waveform measurement switch may be provided, and the electrocardiogram waveform measurement may be started immediately after or when a predetermined time elapses after the pressing (turning ON) of the electrocardiogram waveform measurement electrode.

The communication unit 68 and the communication unit 69 may employ different communication schemes. For example, a general portable information terminal includes a voice input unit (microphone). Thus, for example, the information about electrocardiogram waveform output from one communication unit may be output on sound waves, whereas the information about blood pressure and pulse rate output from the other communication unit may be output on radio waves. Conversely, the information about the electrocardiogram waveform output from one communication unit may be output on radio waves, and the information about blood pressure and pulse rate output from the other communication unit may be output on sound waves.

Preferably, the designed distance between the electrocardiogram waveform measurement electrodes or the reference electrodes arranged in the side surface electrode region is about 20 cm to about 30 cm so that the subject can maintain a relaxed measurement posture. The reason is that when the subject takes a stressful posture, the blood pressure value in the blood pressure measurement increases, and noise due to a change in the myoelectricity of the subject may be reflected on the electrocardiogram waveform.

Figure 7:
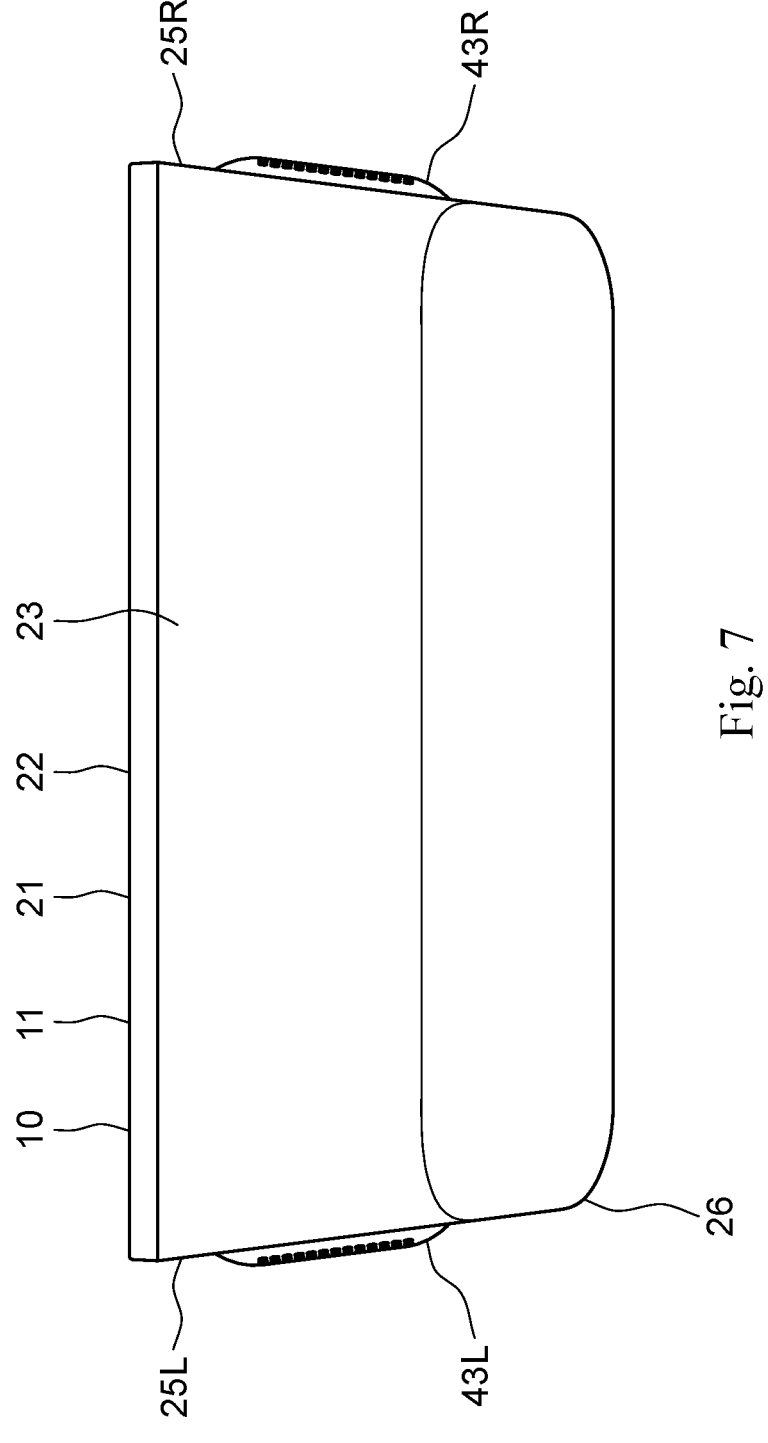
FIG. 7 is a perspective view of the upper-arm type sphygmomanometer main body illustrated in FIG. 1 as viewed from obliquely below.

As illustrated in FIG. 7, the electrocardiogram waveform measurement electrode 43 (the first electrocardiogram waveform measurement electrode 43L and the second electrocardiogram waveform 43R) arranged in the side surface electrode region 42 (the first and the second side electrode regions 42L and 42R) preferably has a surface in a curved form protruding outward. Furthermore, it is preferable that the left and right side surfaces 25 (25L, 25R) are tapered such that the distance therebetween gradually decreases from the upper surface 22 toward the bottom surface 26. The finger 103 other than the thumbs of the left and right hands of the subject 100 is in a form to have the tip portion curved inward in a natural state. Therefore, with the electrocardiogram waveform measurement electrode 43 protruding in a curved shape, the fingertip can be more stably brought into contact with the electrode surface, so that variation in the contact resistance between the finger and the electrode can be reduced. Furthermore, with the left and right side surfaces 25 tapered toward side opposite to the subject 100, the subject 100 can be in a natural posture to touch the electrocardiogram waveform measurement electrodes 43. As a result, a stable electrocardiogram waveform with less noise can be obtained.

The first and the second side electrode regions and the first and second side surface electrodes may extend from the side surfaces to corners connected to the back surface, or may extend into the back surface beyond the corner portion.

As described above, a main body of an upper-arm type sphygmomanometer that measures blood pressure of a subject by using a bag-shaped arm cuff to be wound around an arm of the subject according to an embodiment of the disclosure includes:

a housing;

an electrocardiogram waveform measurement circuit provided inside the housing;

a first electrocardiogram waveform measurement electrode and a second electrocardiogram waveform measurement electrode that are provided on an outer surface of the housing, and are electrically connected to the electrocardiogram waveform measurement circuit; and a first reference electrode electrically connected to the electrocardiogram waveform measurement circuit, wherein the housing includes an upper surface, a front surface, a back surface, and a pair of a first side surface and a second side surface on left and right sides, the first side surface includes a first side surface electrode region, the second side surface includes a second side surface electrode region, the upper surface includes a first upper surface electrode region positioned closer to the first side surface than the second side surface, the first electrocardiogram waveform measurement electrode is provided in the first upper surface electrode region, the second electrocardiogram waveform measurement electrode is provided in the second side surface electrode region, the first reference electrode is provided in the first side surface electrode region, and the first electrocardiogram waveform measurement electrode and the first reference electrode are provided at positions to be simultaneously touchable by one hand of the subject.

With this sphygmomanometer main body, external noise that may otherwise be included in the electrocardiogram waveform can be removed, with one of the left and right reference electrodes touched by the subject's finger. Furthermore, the body motion noise that may be included in the electrocardiogram waveform can be removed with the electrocardiogram waveform measurement electrode and the reference electrode touched with the fingers of the subject in a relaxed state. Thus, a highly reliable electrocardiogram waveform can be obtained in addition to the blood pressure.

The sphygmomanometer main body according another embodiment, further includes a second reference electrode electrically connected to the electrocardiogram waveform measurement circuit, wherein the upper surface includes a second upper surface electrode region positioned closer to the second side surface than the first side surface, the second reference electrode is provided in the second upper surface electrode region, and the second electrocardiogram waveform measurement electrode and the second reference electrode are provided at positions to be simultaneously touchable by one hand of the subject.

With this sphygmomanometer main body, external noise that may otherwise be included in the electrocardiogram waveform can be removed, with both of the left and right reference electrodes touched by the subject's fingers.

A main body of an upper-arm type sphygmomanometer that measures blood pressure of a subject by using a bag-shaped arm cuff to be wound around an arm of the subject according to another embodiment includes:

a housing;

an electrocardiogram waveform measurement circuit provided inside the housing;

a first electrocardiogram waveform measurement electrode and a second electrocardiogram waveform measurement electrode that are provided on an outer surface of the housing, and are electrically connected to the electrocardiogram waveform measurement circuit; and a first reference electrode electrically connected to the electrocardiogram waveform measurement circuit, wherein the housing includes an upper surface, a front surface, a back surface, and a pair of a first side surface and a second side surface on left and right sides, the first side surface includes a first side surface electrode region, the second side surface includes a second side surface electrode region, the upper surface includes a first upper surface electrode region positioned closer to the first side surface than the second side surface, the first electrocardiogram waveform measurement electrode is provided in the first upper surface electrode region, the second electrocardiogram waveform measurement electrode is provided in the second side surface electrode region, the first reference electrode is provided in the first side surface electrode region, and the first electrocardiogram waveform measurement electrode and the first reference electrode are provided at positions to be simultaneously touchable by one hand of the subject.

With this sphygmomanometer main body, external noise that may otherwise be included in the electrocardiogram waveform can be removed, with one of the left and right reference electrodes touched by the subject's finger. Furthermore, the body motion noise that may be included in the electrocardiogram waveform can be removed with the electrocardiogram waveform measurement electrode and the reference electrode touched with the fingers of the subject in a relaxed state. Thus, a highly reliable electrocardiogram waveform can be obtained in addition to the blood pressure.

The sphygmomanometer main body according another embodiment, further includes a second reference electrode electrically connected to the electrocardiogram waveform measurement circuit, wherein the upper surface includes a second upper surface electrode region positioned closer to the second side surface than the first side surface, the second reference electrode is provided in the second upper surface electrode region, and the second electrocardiogram waveform measurement electrode and the second reference electrode are provided at positions to be simultaneously touchable by one hand of the subject.

With this sphygmomanometer main body, external noise that may otherwise be included in the electrocardiogram waveform can be removed, with both of the reference electrodes touched by the subject's fingers.

In the sphygmomanometer main body according to another embodiment, the first upper surface electrode region is positioned closer to the front surface than the first side surface electrode region is, and the second upper surface electrode region is positioned closer to the front surface than the second side surface electrode region is.

With this sphygmomanometer main body, the body motion noise that may be included in the electrocardiogram waveform can be removed because the electrocardiogram waveform measurement electrode and the reference electrode can be stably touched with the fingers of the subject in a relaxed state.

In the sphygmomanometer main body according to another embodiment, the upper surface is inclined upward to be higher toward the back surface from the front surface.

With this sphygmomanometer main body, the body motion noise that may be included in the electrocardiogram waveform can be removed because the electrocardiogram waveform measurement electrode and the reference electrode can be stably touched with the fingers of the subject in a relaxed state.

In the sphygmomanometer main body according to another embodiment, the first side surface electrode region extends in a region connecting the back surface and the first side surface to each other, and the second side surface electrode region extends in a region connecting the back surface and the second side surface to each other.

With this sphygmomanometer main body, the side surface electrodes can be arranged at positions where the subject's finger can easily touch. Thus, the body motion noise that may be included in the electrocardiogram waveform can be removed because the electrodes on the side surfaces can be stably touched with the fingers of the subject in a relaxed state.

In the sphygmomanometer main body according to another embodiment, the first side surface electrode region and the second side surface electrode region are laterally symmetrically provided.

With this sphygmomanometer main body, since the left and right side surface electrodes receive force in opposite directions on the same line of action, body motion noise that may be included in the electrocardiogram waveform can be removed.

In the sphygmomanometer main body according to another embodiment, the first electrocardiogram waveform measurement electrode and the second electrocardiogram waveform measurement electrode are supported by an elastic supporting portion that is made of an elastic and insulating material and fixed to the housing.

With this sphygmomanometer main body, the elastic supporting portion is deformed when the subject's finger comes into contact with the electrocardiogram waveform measurement electrode, so that the subject can recognize that his/her finger is in contact with the electrocardiogram waveform measurement electrode with appropriate force.

In the sphygmomanometer main body according to another embodiment, a surface of at least one of the first electrocardiogram waveform measurement electrode provided in the first side surface electrode region and the second electrocardiogram waveform measurement electrode provided in the second side surface electrode region, is a curved surface protruding outward.

With this sphygmomanometer main body, the body motion noise that may be included in the electrocardiogram waveform can be removed because the electrocardiogram waveform measurement electrode can be stably touched with the fingers of the subject in a relaxed state.

In the sphygmomanometer main body according to another embodiment, a surface of at least one of the first electrocardiogram waveform measurement electrode and the second electrocardiogram waveform measurement electrode has at least one protrusion protruding outward.

With this sphygmomanometer main body, the subject can recognize that his/her finger is in contact with the electrocardiogram waveform measurement electrode with the fingers coming into contact with the protrusion.

In the sphygmomanometer main body according to another embodiment, the housing accommodates an air supply circuit for supplying air to an air bladder accommodated in the arm cuff, an air pump that supplies air to the air bladder through the air supply circuit, a pressure sensor that detects pressure of air in the air supply circuit, and a blood pressure measurement circuit that measures the blood pressure of the subject based on an output from the pressure sensor.

With this sphygmomanometer main body, the electrocardiogram waveform measurement and the blood pressure measurement can be performed at once with the arm cuff connected to the air supply circuit.

An upper-arm type sphygmomanometer according to an embodiment of the present disclosure includes:

a sphygmomanometer main body; and an arm cuff unit that is detachably attached to the sphygmomanometer main body, wherein the sphygmomanometer main body is the sphygmomanometer main body according to the other embodiment, the arm cuff unit includes a belt-shaped arm cuff incorporating an air bladder, and an air tube that has one end connected to the air bladder, and supplies air to the air bladder, the sphygmomanometer main body includes a tube connection portion to which another end of the air tube is detachably connected, the tube connection portion being provided on a surface of the housing, and the tube connection portion is connected to the air supply circuit.

With this upper-arm type sphygmomanometer, the electrocardiogram waveform measurement and the blood pressure measurement can be performed at once with the arm cuff connected to the air supply circuit.

As described above, according to the invention of the present application, a sphygmomanometer main body can be provided with the following features. Specifically, with the subject's finger touching one of the left and right reference electrodes, external noise that may otherwise be included in the electrocardiogram waveform is removed. Furthermore, with the electrocardiogram waveform measurement electrode and the reference electrode touched by the fingers of the subject in a relaxed state, the body motion noise that may be included in the electrocardiogram waveform can be removed. Thus, a highly reliable electrocardiogram waveform can be obtained in addition to the blood pressure.

It is to be noted that the various embodiments described above can be appreciated individually within each embodiment, but the embodiments can be combined together. It is also to be noted that the various features in different embodiments can be appreciated individually by its own, but the features in different embodiments can be combined.

REFERENCE NUMERALS

FIG. 5

34 DISPLAY UNIT

35 REFERENCE ELECTRODE

38 COMMUNICATION SW

39 START/STOP SW

41 PORTABLE INFORMATION TERMINAL

43 ELECTROCARDIOGRAM WAVEFORM MEASUREMENT ELECTRODE

52 AIR BLADDER

62 BLOOD PRESSURE MEASUREMENT CIRCUIT

63 ELECTROCARDIOGRAM WAVEFORM MEASUREMENT CIRCUIT

65 AIR PUMP

66 DISCHARGE VALVE

67 PRESSURE SENSOR 68, 69 COMMUNICATION UNIT

FIGS. 8A,8B, 9A, 9B

VOLTAGE

TIME [sec]

The invention claimed is:

1. A sphygmomanometer main body of an upper-arm type sphygmomanometer that measures blood pressure of a subject by using a bag-shaped arm cuff to be wound around an arm of the subject, the sphygmomanometer main body comprising:

a housing configured to be placed on a table, the housing comprising:

a bottom surface to face the table, an upper surface positioned opposite to the bottom surface, a front surface extending from the bottom surface to the upper surface on a front side of the housing, a back surface extending from the bottom surface to the upper surface on a back side of the housing, and a pair of a first side surface and a second side surface extending from the bottom surface to the upper surface on left and right sides of the housing, wherein the upper surface has an upward inclination to be higher toward the back surface from the front surface, the upper surface is delimited, by a step, into a terminal placement portion occupying a region separated from the front surface with respect to a direction along the upward inclination and a rest portion other than the terminal placement portion, the terminal placement portion extending flatly along the upward inclination and having a predetermined size and shape for a portable information terminal including a display to be placed, the step lowers from the rest portion to the terminal placement portion and has a U-shaped configuration that surrounds a front side, a left side, and a right side of the terminal placement portion and not a back side of the terminal placement portion, such that the terminal placement portion is open upward and backward, the first side surface is provided with a first electrode configured to measure a potential with the first electrode touched by one of second to fifth fingers of one hand of the subject, the second side surface is provided with a second electrode configured to measure a potential with the second electrode touched by one of second to fifth fingers of the other hand of the subject, a first region of the rest portion of the upper surface positioned closer to the first side surface than the second side surface is provided with a third electrode configured to measure a potential with the third electrode touched by a first finger of the one hand of the subject, a second region of the rest portion of the upper surface positioned closer to the second side surface than the first side surface is provided with a fourth electrode configured to measure a potential with the fourth electrode touched by a first finger of the other hand of the subject, an electrocardiogram waveform measurement circuit, a transmission unit and a processor are provided inside the housing, the electrocardiogram waveform measurement circuit is configured to obtain electrocardiogram waveform information representing an electrocardiogram waveform from a potential difference between the potential input to the first electrode and the potential input to the third electrode, or a potential difference between the potential input to the second electrode and the potential input to the fourth electrode, the transmission unit is configured to be capable of transmitting the electrocardiogram waveform information, and the processor is configured to transmit, during a measurement, the electrocardiogram waveform information obtained by the electrocardiogram waveform measurement circuit to the portable information terminal placed on the terminal placement portion through the transmission unit, such that the electrocardiogram waveform is displayed on the display of the portable information terminal.

2. The sphygmomanometer main body according to claim 1, wherein the electrocardiogram waveform measurement circuit removes a noise from the electrocardiogram waveform by subtracting the potential input to the third electrode as a reference potential from the potential input to the first electrode in case of using the first electrode and the third electrode or by subtracting the potential input to the fourth electrode as a reference potential from the potential input to the second electrode in case of using the second electrode and the fourth electrode.

3. The sphygmomanometer main body according to claim 2, wherein the first electrode and the second electrode are supported by an elastic supporting portion that is made of an elastic and insulating material and fixed to the housing.

4. The sphygmomanometer main body according to claim 2, wherein a surface of at least one of the first electrode and the second electrode is a curved surface protruding outward.

5. The sphygmomanometer main body according to claim 2, wherein a surface of at least one of the first electrode and the second electrode has at least one protrusion protruding outward.

6. The sphygmomanometer main body according to claim 1, wherein the electrocardiogram waveform measurement circuit removes a noise from the electrocardiogram waveform by subtracting the potential input to the first electrode as a reference potential from the potential input to the third electrode in case of using the first electrode and the third electrode or by subtracting the potential input to the fourth electrode as a reference potential from the potential input to the second electrode in case of using the second electrode and the fourth electrode.

7. The sphygmomanometer main body according to claim 1, wherein the terminal placement portion has a back end protruding backward along the upward inclination beyond the back surface of the housing.

8. The sphygmomanometer main body according to claim 1, wherein the first electrode and the second electrode are laterally symmetrically provided.

9. The sphygmomanometer main body according to claim 1, wherein the housing accommodates:
an air supply circuit for supplying air to an air bladder accommodated in the bag-shaped arm cuff;

an air pump that supplies the air to the air bladder through the air supply circuit;

a pressure sensor that detects pressure of the air in the air supply circuit; and a blood pressure measurement circuit that measures the blood pressure of the subject based on an output from the pressure sensor.

10. An upper-arm type sphygmomanometer comprising:

the sphygmomanometer main body according to claim 9; and an arm cuff unit that is detachably attached to the sphygmomanometer main body, wherein the arm cuff unit comprises:
the bag-shaped arm cuff accommodating the air bladder; and an air tube that has one end connected to the air bladder, and supplies the air to the air bladder, the sphygmomanometer main body comprises a tube connection portion to which another end of the air tube is detachably connected, the tube connection portion being provided on a surface of the housing, and the tube connection portion is connected to the air supply circuit.

11. A method for measuring an electrocardiogram waveform of a subject by using a sphygmomanometer having a sphygmomanometer main body, the sphygmomanometer main body comprising:

a housing configured to be placed on a table, the housing comprising:

a bottom surface to face the table, an upper surface positioned opposite to the bottom surface, a front surface extending from the bottom surface to the upper surface on a front side of the housing, a back surface extending from the bottom surface to the upper surface on a back side of the housing, and a pair of a first side surface and a second side surface extending from the bottom surface to the upper surface on left and right sides of the housing, wherein the upper surface has an upward inclination to be higher toward the back surface from the front surface, the upper surface is delimited, by a step, into a terminal placement portion occupying a region separated from the front surface with respect to a direction along the upward inclination and a rest portion other than the terminal placement portion, the terminal placement portion extending flatly along the upward inclination and having a predetermined size and shape for a portable information terminal including a display to be placed, the step lowers from the rest portion to the terminal placement portion and has a U-shaped configuration that surrounds a front side, a left side, and a right side of the terminal placement portion and not a back side of the terminal placement portion, such that the terminal placement portion is open upward and backward, the first side surface is provided with a first electrode configured to measure a potential with the first electrode touched by one of second to fifth fingers of one hand of the subject, the second side surface is provided with a second electrode configured to measure a potential with the second electrode touched by one of second to fifth fingers of the other hand of the subject, a first region of the upper surface positioned closer to the first side surface than the second side surface is provided with a third electrode configured to measure a potential with the third electrode touched by a first finger of the one hand of the subject, a second region of the upper surface positioned closer to the second side surface than the first side surface is provided with a fourth electrode configured to measure a potential with the fourth electrode touched by a first finger of the other hand of the subject, an electrocardiogram waveform measurement circuit is provided inside the housing, the electrocardiogram waveform measurement circuit is configured to obtain electrocardiogram waveform information representing an electrocardiogram waveform from a potential difference between the potential input to the first electrode and the potential input to the third electrode, or a potential difference between the potential input to the second electrode and the potential input to the fourth electrode, the first side surface has a first height equal to or greater than a combined width of the second to fifth fingers of the one hand of the subject, and extends in a front and rear direction for a first length longer than all of the second to fifth fingers of the one hand of the subject, and the second side surface has a second height equal to or greater than a combined width of the second to fifth fingers of the other hand of the subject, and extends in the front and rear direction for a second length longer than all of the second to fifth fingers of the other hand of the subject, wherein the method comprises:

in a state where the housing is placed on the table, touching the first electrode by the one of the second to fifth fingers of the one hand of the subject, placing the fifth finger of the one hand of the subject on the table, and extending all of the second to fifth fingers of the one hand of the subject in the front and rear direction along the first side surface, and touching the second electrode by the one of the second to fifth fingers of the other hand of the subject, placing the fifth finger of the other hand of the subject on the table, and extending all of the second to fifth fingers of the other hand of the subject in the front and rear direction along the second side surface, and then obtaining, by the electrocardiogram waveform measurement circuit, the electrocardiogram waveform information representing the electrocardiogram waveform from a potential difference between the potential input to the first electrode and the potential input to the third electrode, or a potential difference between the potential input to the second electrode and the potential input to the fourth electrode.

* * * * *